United States Patent
Siess

(10) Patent No.: US 9,056,124 B2
(45) Date of Patent: Jun. 16, 2015

(54) METHOD FOR THE TREATMENT OF TUBERCULOSIS

(71) Applicant: Harold Edward Siess, Ooltewah, TN (US)

(72) Inventor: Harold Edward Siess, Ooltewah, TN (US)

(*) Notice: Subject to any disclaimer, the term of this patent is extended or adjusted under 35 U.S.C. 154(b) by 0 days.

(21) Appl. No.: 14/149,180

(22) Filed: Jan. 7, 2014

(65) Prior Publication Data

US 2014/0193371 A1 Jul. 10, 2014

Related U.S. Application Data

(60) Provisional application No. 61/956,172, filed on Jan. 7, 2013.

(51) Int. Cl.
| | |
|---|---|
| *A61K 31/075* | (2006.01) |
| *A61K 35/76* | (2015.01) |
| *A61K 33/36* | (2006.01) |
| *A61K 33/18* | (2006.01) |
| *A61K 35/74* | (2015.01) |
| *A61K 31/00* | (2006.01) |
| *A61K 33/24* | (2006.01) |
| *A61K 33/34* | (2006.01) |
| *A61K 33/38* | (2006.01) |

(52) U.S. Cl.
CPC .................. *A61K 35/76* (2013.01); *A61K 33/36* (2013.01); *A61K 33/18* (2013.01); *A61K 35/74* (2013.01); *A61K 31/00* (2013.01); *A61K 33/24* (2013.01); *A61K 33/34* (2013.01); *A61K 33/38* (2013.01)

(58) Field of Classification Search
CPC ..................................................... A61K 31/075
See application file for complete search history.

(56) References Cited

PUBLICATIONS

Svachulova, "Effect of L-ascorbic acid on the growth and metabolism of *Mycobacterium tuberculosis*," Rozhledy Tuberk. 16:203-206, 1956, Abstract only.*
Scoz et al., "Hypovitaminosis C and experimental tuberculosis," Bollettino-Societa Italiana di Biologia Sperimentale 11:909-911, 1936, Abstract only.*
Awotedu et al., "Ascorbic acid deficiency in pulmonary tuberculosis," East African Medical Journal 61(4):283-287, 1984, Abstract only.*
Selmiciu et al., English abstract of Romanian Patent No. 53839, 1971.*

* cited by examiner

*Primary Examiner* — Rosanne Kosson
(74) *Attorney, Agent, or Firm* — Luedeka Neely Group, P.C.

(57) ABSTRACT

A method for preventing and treating one or more disease states including the steps of altering the diet of an individual and then administering a drug to the individual. Plasma vitamin C level is reduced from a first level to a second level that is lower than the first level, such that a pharmacological response of the body of the individual to a drug at the first level is different from the pharmacological response of the body of said individual to the drug at the second level.

3 Claims, No Drawings

METHOD FOR THE TREATMENT OF TUBERCULOSIS

CROSS-REFERENCE TO RELATED APPLICATION

This application claims the benefit of U.S. Provisional Application No. 61/956,172, filed Jan. 7, 2013.

FIELD

This invention relates to the field of cancer treatment methods. More particularly, this invention relates to a method for treating cancer and pathological lesions, and other related diseases by first lowering the plasma vitamin C level of the blood to abnormally low levels for altering either the pharmacological response to a drug or for altering the immune response to a therapeutic infection or by lowering the concentration of ascorbic acid and/or its oxidized or reduced derivatives within a pathological lesion for initiating a scurvy induced phogocytotic readsorption of the pathological lesion.

INTRODUCTION

It is currently held from epidemiological studies that diet can alter the incidence of cancer, including breast cancer. In particular, it is currently held from such studies that a polyunsaturated fatty acid enriched diet correlates with a reduction in cancer rates. It has been theorized that breast cancer cells can be sensitized to the cytotoxic effects of anti-cancer agents by the modification of the lipid rafts by incorporating fatty acid supplementation into the diet of cancer patients. See for example B. Chénais and V. Blanckaert "The Janus Face of Lipids in Human Breast Cancer: How Polyunsaturated Fatty acids Affect Tumor Cell Hallmarks" Int. J. of Breast Cancer Vol. 2112 Article ID 712536

It is not currently held that the reduction in the above noted rates of cancer were, in any degree, brought about by contracting an erysipeloid infection by the handing of the fish that provided the polyunsaturated fatty acid enriched diet.

It was known in the late 1800s that the Jews in New York did not suffer from either cancer or tuberculosis to the extent that the general population did. This was, and still is, believed by many to be due to their unique diet. No one has attributed the unique exemption of the Jews at that time from either cancer or tuberculosis to the consumption of a clathrate forming substance in the form of ether that was used at that time to give fake olive oil both its smell and flavor. It was, however, known that they did use olive oil much like we use butter today.

It was known in the 1800s that miners in England and printers in Germany had low rates of cancer and that the miners in England had low rates of tuberculosis and lived till a "green old age." No explanation was given at the time or since. In particular no one has related these phenomena to the presence of clathrate forming substances in the air the miners or printers breathed.

It was known to use ether in the treatment of tuberculosis in the 1800s. However, no limitations on diet were given at that time. In particular, there was not limitation on the amount of vitamin C consumed during the treatment process. In addition, there were no medicines given to reduce the level of ascorbic acid or its reduced or oxidized derivatives in the blood before or during the treatment process. In addition, it was not taught to inoculate the patient with an infection for reducing the plasma vitamin C level during the treatment using ether.

It was believed since ancient times that a sea voyage had a therapeutic effect on tuberculosis. The ancients largely held these effects to be due to the "airs" that were to be found over the open ocean waters. Later on and up to the present, these effects were believed to be due to the fresh air and perhaps the salt particles contained in the air over the open ocean waters. It has not been theorized that humans have evolved to fight off tuberculosis by seasonally going through scurvy or near scurvy condition when plants containing vitamin C were scarce.

It is known that data was collected in the later part of the 1800s that indicated the geographical location of the rates of cancer throughout the world. However, no correlation has been made between the geographical locations having low cancer rates and a seasonal reduction in the about of vitamin C consumed by the population. In addition no medical theory has been put forth that humans have evolved to undergo a seasonal reduction in the level of vitamin C consumed as a way of combating chronic diseases, such as, for example, cancer, tuberculosis and the like. It is also known that data was collected in the latter part of the 1800s on the prevalence of scurvy throughout the world. However, no correlation has been made between the geographical locations having low cancer rates with those geographical locations demonstrating a high incidence of scurvy.

It is known from data published in the 1800s that butchers, slaughterhouse workers and tanners had reduced rates of tuberculosis. However, no correlation has been made between the reduction in the rates of tuberculosis along these professions and the occurrence of an erysipeloid infection. Still further, it has not been shown that the vitamin C reducing potential of an erysipeloid infection can be correlated with the reduced rates of tuberculosis among these professionals. It is known since ancient times that during scurvy new growths such as recent scar tissue and the like are often reabsorbed by body. However, scurvy has not been considered useful in the treatment of diseases that give rise to new growths such as for example, cancer, tuberculosis, lupus and some forms of insanity. As used herein such processes will be termed scurvy induced phagocytosis.

It was generally held since ancient times that an erysipelas infection could be of a salutary nature in a number of diseases. However, no correlation has ever been made between the vitamin C reducing potential of an erysipelas infection and its curative effects. Therefore, it was unknown in the past to reduce the level of vitamin C in either the tissues under consideration or the blood level before and/or during the use of an erysipelas infection. It was also not realized or taught that it was an erysipelas infection in the form of a 'scorbutic erysipelas' infection that gave rise to its curative effects by scurvy induced phagocytotic processes. After a strain of the bacteria responsible erysipelas was first cultured an attempt to cure a patient with cancer by the inoculation of the bacteria was attempted. No attempt was made to reduce the level of vitamin C prior and/or during the treatment process. The attempt failed with loss of the life of the patient. In addition, no clathrate forming substance such as ether was used during the treatment process to alter the course of the infection process or the outcome of the treatment.

In addition, the above noted researchers did teach the use of other skin and soft-tissue infections that involve the lymphatics, such as those that cause erysipeloid and/or cellulitis as a method of treatment.

What is needed, therefore, is an improved method for treating and preventing cancer and related diseases, based on the correlations between both cancer and tuberculosis rates and the use of:

(1) clathrate forming substances as a means of preventing cancer, tuberculosis and related diseases;
(2) the reduction in the level of vitamin C in the diet prior to and/or during cancer and/or tuberculosis treatment; and/or
(3) the contraction of an infection for lowering the level of vitamin C in the patient during treatment process. In particular, what is needed is a treatment plan for the prevention and/or cure of cancer and/or tuberculosis using these three methods together.

SUMMARY

The above and other needs are met by a method for preventing and treating cancer and other pathological lesions. The method comprises the step of lowering the concentration of ascorbic acid and/or its oxidized or reduced derivatives within a pathological lesion for initiating a scurvy induced phagocytotic readsorption of the pathological lesion. The concentration of ascorbic acid and/or its derivatives can be reduced by either diet and/or the administration of an anti-vitamin C agent to produce a fulminating scurvy condition at the site of the pathological lesion.

In one form of the invention wherein the anti-vitamin C agent is a pathological microbe, a clathrate forming substance, which can be in the form of an anesthetic agent such as ether is administered during the treatment process for controlling the immune response of the body to the microbe.

In another form of the present invention, the concentration of ascorbic acid and/or its oxidized or reduced derivatives is reduced within a pathological lesion for altering the pharmacological response of the cells comprising the lesion to a drug. The method includes the steps of altering the diet of an individual and then administering a drug to the individual. In particular, the plasma vitamin C level is reduced from a first level to a second level that is lower than the first level, such that a pharmacological response of the body of said individual to a drug at the first level is different from the pharmacological response of the body of said individual to the drug at the second level In certain embodiments, the plasma vitamin C level is maintained at the second level for at least one month. In some embodiments, the method further includes the step of administering an anti-vitamin C agent to the individual prior to administering the drug to reduce the plasma vitamin C level for accelerating the rate at which ascorbic acid or one or its reduced or oxidized forms is removed from the body. In certain preferred embodiments, the anti-vitamin C agent is selected from the group consisting of a metal substance, a metalloid substance, an organic agent, an oxidizing agent, an infectious agent, and arsenic. In some embodiments, the method may further include the step of measuring the plasma vitamin C level of said individual prior to administering the drug. According to some embodiments, the drug is an agent for altering a plurality of lipid rafts on a cell membrane in a plurality of diseased cells within said individual. In some embodiments, the drug includes a clathrate forming substance.

It is an object of the present invention to provide a method for the treatment and prevention of cancer and related diseases. It is a particular object of the present invention to provide for the treatment of lipid raft dependent diseases. Still further, it is an object of the present invention to provide for an enhanced method for the removal of cholesterol from unhealthy tissues for either (1) the treatment of various disease states or (2) as a means or rejuvenating the body. Yet still further, the present invention provides for medicinal agents for the prevention of cancer, tuberculosis and other lipid raft dependent diseases in the form of clathrate forming substances.

DETAILED DESCRIPTION

"Subclinical scurvy" is generally defined as a condition wherein low levels of vitamin C are present in the blood stream but not to a point sufficient to present either the early symptoms of weakness and lassitude or the later symptoms of swelling of the legs and arms, softening of the gums, hemorrhages from the nose and gums and under the skin, and extensive degeneration of bone and cartilage. Individuals suffering from subclinical scurvy are generally termed "scorbutic." In the present invention, a scorbutic patient will be defined a patient who, upon the contraction of an infectious disease and/or by the consumption of a vitamin C lowering substance, develops scurvy.

Additionally, as is known in the art, scorbutic individuals are highly susceptible to infection. In scorbutic individuals having a marginal vitamin C intake, various infective agents, and certain chemical substances are known to be able to convert a case of subclinical scurvy, where the symptoms are relatively inconspicuous, into what is known as a "fulminating scurvy." "Fulminating" means to happen with lighting speed. As used herein, a "fulminating scurvy" will be defined as a scurvy condition of the blood and/or various other tissues brought about by either an infection or a biological and/or chemical agent. For example, it is known in the art, that both diphtheria and erysipelas may bring about a fulminating scurvy. In addition, it is also known in the art, that the toxin in the pertussis vaccine can often throw a child into a fulminating scurvy to a point where hemorrhagic complications present themselves. In this case, the fulminating scurvy is brought about by consumption of vitamin C at enormous rates in the neutralization process of the pertussis toxin.

There are a number of theories that can be developed as to why cancer, tuberculosis and other lipid raft-dependent diseases can be either prevented and/or treated by:
1. Reducing the level of vitamin C in either the blood stream or the tissues under consideration; and
2. By the use of clathrate substances during the treatment process.

The inoculation of infective agents for lowering the plasma vitamin C level in the present invention is not limited to any of these theories that may be developed or are presented herein but is rather limited only by the claims presented. However, as an aid to those skilled in the art, I will state the following;

A. I think that scurvy may operate in combating lipid-dependent diseases such as cancer, tuberculosis other new growth diseases, and the like by altering the orientation of one or more receptor proteins held within the lipid rafts in such a manner as to initiate scurvy-induced phagocytosis.

B. I think that an infection that brings about a reduction in the level of vitamin C in either the tissues under consideration and/or blood level may also work by exciting the immune response involved in the scurvy-induced phagocytosis process.

C. I think that clathrate-forming substances also combat lipid-dependent diseases by altering the orientation of one or more receptor proteins held within the lipid rafts.

D. I think that humans have evolved to undergo scurvy as a means of combating certain chronic disease states such as tuberculosis and cancer and that the seasonal variation in the level of vitamin C at one time helped regulate the breeding cycle of humans. However, as just stated, these theories are not meant to define the scope and limitations of the present invention.

In one embodiment of the present invention, the diet of the individual to be treated is first altered for lowering the plasma vitamin C level to alter the pharmacological response of the body to a drug such as, for example and in no way limiting the present invention to any particular drug, a clathrate-forming substance. In one form of the invention, the clathrate-forming substance is in the form of an anesthetic agent. In certain other embodiments, a substance, of a type well known in the art is given to the individual for quickly lowering the plasma vitamin C level of the individual and for preferably providing a fulminating scurvy condition.

The plasma vitamin C level of the blood and/or other tissues is then measured to determine if the vitamin C content is low enough for bringing forth the symptoms of scurvy for altering the pharmacological response to the drug that is to be given. If so, the drug is then administered to the individual for preventing or treating one or more disease states. In other embodiments, one or more microbe for either preventing or treating one or more disease states is administered under scurvy conditions in place of or in addition to a drug for altering the therapeutic action of the microbe. In one from the present invention, the microbe is selected from the group comprising those that cause a skin and soft tissue infection such as erysipelas, erysipeloid and/or cellulitis.

In the method of treatment of the present invention, the dietary intake of vitamin C for the patient is first reduced to a degree lower than normal for a sufficient time for altering the pharmacological response to a drug. A sufficient time may include, for example, a month.

In addition to the vitamin C-restricted diet, it is preferred that one or more agents, hereinafter referred to as "anti-vitamin C agents," for lowering the blood plasma level of vitamin C be administered to the patient for accelerating the reduction of vitamin C in the blood. The anti-vitamin C agent can be selected from the group comprising, a substance comprised of a metal or metalloid, an organic agent, an oxidizing agent, an infectious agent, or arsenic. For example, the substance comprised of metal may include, but is not limited to, copper, lead, silver, gold, and antimony.

As is well known in the art, the level of vitamin C a particular patient has is highly dependent on a number of factors including the past consumption of vitamin C containing foods. In the preferred embodiment of the present invention, the patient would be given one or more anti-vitamin C agents in small doses that would be increased according to the individual patient's response. Of course, several blood samples will have to be drawn in order to come to the right dose but such things are expected in the art and cannot be otherwise calculated. In the preferred embodiment of the present invention, the level of both the anti-vitamin C agent and the plasma level of vitamin C is taken on a daily basis for determining the dosage regime necessary to create and maintain a fulminating scurvy condition.

The organic agent may include, but is not limited to, bacterial toxins, such as for example, a diphtheria toxin that is injected. The oxidizing agent may be, but is not limited to, iodine that is given by mouth. The infectious agent may include, but is not limited to, a virus such as the common cold virus that would be injected into the patient.

In one form of the present invention, before the a therapeutic agent is given, the level of plasma vitamin C is sustained at a sufficiently low level for the development of scurvy or to alter the cholesterol content of the lipid rafts. In certain embodiments, before the therapeutic agent is given, the plasma vitamin C level is held below normal levels until the early signs of scurvy are present, including, but not limited to, a feeling of general weakness, a leveling off of the HDL level of the blood, a scurvy-associated pathological change in one or more cell types in the body. Put differently, prior to the inoculation process, the level of vitamin C in the blood would be reduced to at least a subclinical scurvy level.

If the anti-vitamin C agent comprises an organic compound that is a bacterium, the inoculation of the bacteria should be given directly over the site to be treated. For example, if the breast were to be treated, then the inoculation would be given on the skin at that site and if the brain is to be treated then the scalp should be inoculated. In addition, the nearby lymphatic vessels may also be inoculated. Of course the site should be sterilized before the inoculation process begins. It would be convenient to chose one or more strains of bacteria that are known to be highly responsive to known anti-bacterial drugs and/or antibiotics in case the infection should get out of hand. During the treatment, an iron-fortified diet should be provided in order to keep the bacteria growing and the vitamin C level should be monitored.

The clathrate-forming substances and/or arsenic may also be used to lower the immune response in order for the bacteria to grow. In the case of the clathrate forming substances, these can be given three or four times a day in doses less than needed to bring about a complete anesthetic response. The arsenic should be given in amounts insufficient to cause death. The therapy should continue until the problem is resolved.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for the treatment of a pathogenic new tuberculosis lesion in a patient, said method comprising the step of lowering the concentration of ascorbic acid in said pathogenic new tuberculosis lesion for reducing the size thereof by scurvy induced phagocytosis, wherein a therapeutically effective amount of an ascorbic acid inhibitor is administered to the patient.

2. The method according to claim 1, wherein the ascorbic acid inhibitor is a clathrate forming substance in the form of an anesthetic agent.

3. The method according to claim 2, wherein said anesthetic agent is an ether compound.

* * * * *